United States Patent
Guan et al.

(10) Patent No.: US 6,897,298 B2
(45) Date of Patent: May 24, 2005

(54) METHOD FOR EXTRACTING A COMPOUND FROM A GINSENG SPP. PLANT, GINSENG OR PSEUDO-GINSENG

(75) Inventors: Yongyuan Guan, Guangdong Province (CN); Fulin Fan, Guangdong Province (CN)

(73) Assignees: Guangdong Taihe Biopharmaceutical Co., Ltd., Guangzhou (CN); Dept. of Science & Tech Develop, Guangzhou (CN)

( * ) Notice: Subject to any disclaimer, the term of this patent is extended or adjusted under 35 U.S.C. 154(b) by 0 days.

(21) Appl. No.: 10/169,397

(22) PCT Filed: Jan. 3, 2001

(86) PCT No.: PCT/CN01/00006

§ 371 (c)(1),
(2), (4) Date: Oct. 29, 2002

(87) PCT Pub. No.: WO01/49704

PCT Pub. Date: Jul. 12, 2001

(65) Prior Publication Data

US 2003/0148962 A1 Aug. 7, 2003

(51) Int. Cl.[7] .......................... C07J 17/00; A01N 45/00
(52) U.S. Cl. ................ 536/6; 536/5; 536/6.3; 514/26; 424/728
(58) Field of Search .......................... 514/26; 424/728; 536/5, 6, 6.3

(56) References Cited

U.S. PATENT DOCUMENTS

| | | | | |
|---|---|---|---|---|
| 3,901,875 A | * | 8/1975 | Park .............................. | 536/5 |
| 4,317,816 A | * | 3/1982 | Arichi et al. .................. | 514/26 |
| 4,339,442 A | * | 7/1982 | Takemoto et al. ............ | 514/26 |
| 5,679,806 A | * | 10/1997 | Zheng et al. ................. | 549/403 |

FOREIGN PATENT DOCUMENTS

GB        2179042 A   *   2/1987

OTHER PUBLICATIONS

Kasai, Ryoji, et al., Glycosides from Chinese Medicinal Plant, *Hemsleya panacis–scandens*, and Structure–Taste Relationship of Cucurbitane Glycosides, Chem. Pharm. Bull. (1988), 36(1), 234–243.

Paper from a Search Report for PCT/CN01/00006, published Apr. 26, 2001.

* cited by examiner

Primary Examiner—James O. Wilson
Assistant Examiner—Traviss C. McIntosh, III
(74) Attorney, Agent, or Firm—Millen White Zelano & Branigan, P.C.

(57) ABSTRACT

This invention discloses a compound (I) of the following formula. This invention also includes a method for extracting the compound (I), and a pharmaceutical composition containing the compound (I). The extracting method includes the following steps: taking the corpus radicis and/or radix fibrosa of a ginseng spp. plant—ginseng or pseudo-ginseng, extracting with industrial alcohol and n-butanol to extract the total saponins, and then purifying by silicon gel column chromatography and reversed phase column chromatography to obtain the compound (I). The compound (I) and pharmaceutical composition can be used to cure acute ischemic cerebral-vascular diseases.

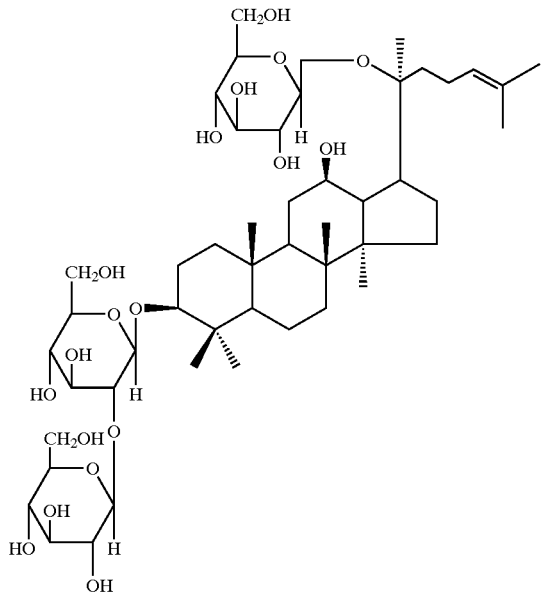

13 Claims, No Drawings

METHOD FOR EXTRACTING A COMPOUND FROM A GINSENG SPP. PLANT, GINSENG OR PSEUDO-GINSENG

FIELD OF INVENTION

The invention relates to a compound, especially a natural compound extracted from ginseng or pseudo-ginseng. The invention also relates to a method of extracting the compound and a pharmaceutical composition containing the compound, which can be used to treat ischemic cerebral-vascular diseases.

BACKGROUND OF THE INVENTION

Ischemic cerebral-vascular diseases are those which affect human health seriously. Its incidence shows a trend of increasing gradually. When a cerebral ischemia occurs, there is rapid appearance of energy metabolic obstruction for brain tissue cells, thereby causing release of excitatory neurotransmitter by neurotermini, which is mainly glumatic acid. Then, NMDA and non-NMDA acceptors are activated, causing a series of pathological changes which lead to cerebral injury and infarction. The fact that acceptors are activated can promote $Ca^{2+}$ internal flow in large amount, while $Ca^{2+}$ overload in cells is a key factor and common channel making cerebrum die. When blood supply is resumed in ischemic cerebral tissues, the reperfusion injury can happen. This kind of cerebral injury, resulted after ischemic cerebral tissue is reperfused, is another way of forming cerebral infarction, and it is generally related with increase of $Ca^{2+}$ internal flow and overload. The fact of $Ca^{2+}$ overload, large amount of $Na^+$ internal flow, and oxygen radicals increase in cells can also cause apoptosis of neurocytes, which is an important form for ischemic cerebral cell necrosis, and is a mechanism of forming cerebral infarction.

At present, there is still no ideal drug for treatment of acute ischemic cerebral-vascular diseases (acute ischemic cerebral apoplexy, and acute cerebral infarction). Aiming at the above-mentioned mechanism of morbidity, the usually used method is application of thrombolytics (such as t-PA, etc.) or fibrinolytic drugs (such as snake venom plasmin and ancrode, etc) at early or very early stage of illness. Thrombolysis can resume blood supply to ischemic area of cerebral tissue. However, along with the resuming of blood supply to ischemic areas, it is inevitable to have cerebral cell ischemic/reperfusion injuries. The effect of treatment is still to be evaluated. In addition, brain protection medicine is clinically used to block different mechanisms of cell necrosis after ischemia, and to lengthen survival ability of cells. It can also be used for prevention for patients in critical condition and for recovery of neuronal functions at late stage so as to achieve goals of treatment. This filed is a hot one for current research. At present, available brain protection drugs are as follows. 1) $Ca^{2+}$ channel antagonist: This kind of drugs achieve goals of treatment by means of obstructing electric voltage dependant $Ca^{2+}$ channel, suppressing cell $Ca^{2+}$ internal flow, and relieving $Ca^{2+}$ overload in cells so as to achieve goals of treatment. Clinically applied drugs are Nimodipine, and Flunarizine. But for acute ischemic cerebral-vascular diseases, $Ca^{2+}$ overload, that causes cerebral tissue injuries, is mainly related with $Ca^{2+}$ channel controlled by acceptors. So, effect of treatment with this kind of blocking electric voltage dependent $Ca^{2+}$ antagonist drugs are still to be proved. 2) Drugs, stabilizing cell membrane: citicoline, the cure effect of which is to be proved. As to other brain protection drugs, like glutamic antagonist, $Na^+$ channel antagonist, $\gamma$-amino-butyric acid reinforcing agent, etc, although there is certain theoretical basis, their cure effects have not been proved with clinical research.

Ginseng and pseudo-ginseng are precious Chinese traditional medicine. They are used to cure diseases related to "blood stasis diseases", such as coronary heart diseases, migraine, etc. Good cure effects are achieved. They are used as medicine to improve blood circulation and eliminate stasis. But there was not much research on effective ingredients curing acute ischemic cerebral-vascular diseases, and there was no way to understand the mechanism of their curing "blood stasis diseases".

An object of the invention is to overcome the disadvantage that currently there is no drug to cure acute ischemic cerebral-vascular diseases with good cure effects and little toxic side effects, and provide a drug, which can cure acute ischemic cerebral-vascular diseases with good cure effects and little poisonous side-effects at the same time.

Another object of the invention is to provide a compound extracted from ginseng and pseudo-ginseng as well as a method for extracting the compound. The compound shall have effects in terms of anti-cerebral ischemia/reperfusion injury, and curing ischemic cerebral-vascular diseases.

Still another object of the invention is to provide a pharmaceutical composition for treatment of ischemic cerebral-vascular diseases, wherein the composition contains the above mentioned compound.

BRIEF DESCRIPTIONS OF THE INVENTION

According to one aspect of the invention, it provides a compound having the following formula, its chemical name is 20-(S)-protopanaxadiol-3-[O-$\beta$-D-glucopyranosyl (1→2)-$\beta$-D-glucopyranosyl]-20-O-$\beta$-D-glucopyranoside:

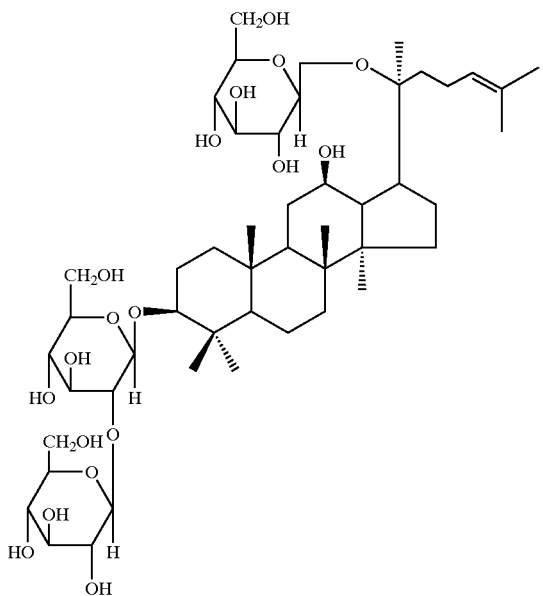

According to another aspect of the invention, it provides a method for extracting the above-mentioned compound, which comprising the following steps:

(1) Taking the corpus radicis and/or radix fibrosa of a ginseng spp. plant—ginseng or pseudo-ginseng, crushing the roots, cold extracting once with industrial alcohol, and hot extracting 0~3 times, after concentration extracting with n-butanol to obtain coarse total saponins;

(2) First separating the coarse total saponins with gradient elution solutions by silicon gel column chromatography, and then concentrating the desired fraction to obtain a concentrate in the form of decocted paste; and (3) Dissolving the concentrate with appropriate amount of methanol, separating and purifying the solution with gradient elution solutions on a reversed phase column, and collecting the desired fraction; recovering methanol from the collected fraction, and allowing it to stand for more than 24 hrs to separate out a white precipitate, and then drying the precipitate to obtain a single substance with high purity.

According to yet another aspect, it provides a pharmaceutical comopsition containing the above-mentioned compound.

DETAIL DESCRIPTION OF THE INVENTION

This invention is implemented as follows.

The name of the compound of the invention [hereinafter referred to as compound (I)]is: 20-(S)-protopanaxadiol-3-[O-β-D-glucopyranosyl (1→2)-β-D-glucopyranosyl]-20-O-β-D-glucopyranoside. Its structure is shown above.

The extracting process of this invention are mainly as follows:

1. Take the corpus radicis and/or radix fibrosa of a ginseng spp. plant—ginseng or pseudo-ginseng. Crush the roots. Do cold extraction once with industrial alcohol, and hot extraction 0~3 times. Combine the filtrates; after recovering ethanol, to extracting coarse total saponins with n-butanol. The ginseng spp. Plant includes North America ginseng.

2. First separate the coarse total saponins with gradient elution solution through silicon gel column chromatograph. Elution solutions are prepared with different proportions of chloroform (85%–60%)-methanol (15%–30%)-water (0%–10%), and gradient elution is carried out. Take ⅓~⅕ of column volume as one portion to collect eluate, and test it with TLC. Collect ingredients having $R_f$ values similar to the control one. After combining, recover the solvent, and obtain a concentrate in the form of decocted paste.

3. After dissolving the concentrate in the form of decocted paste with appropriate amount of methanol, separate and purify it with gradient elution solution on $C_8$~$C_{18}$ is reversed phase column chromatograph 1~2 times. If gradient elution is carried out using elution solutions of different proportions of methanol (50%–100%)-water (0%–50%), take ⅓~⅕ of column volume as one portion of eluate, test it with TLC, and collect the desired ingredients. After the first use of reversed phase column chromatograph, the purity of the single substance can reach 90%. After the second use of reversed phase column chromatograph, the purity of the single substance can reach 95%, and the best is more than 98%. After recovering methanol from the collected eluate, allow it to stand for more than 24 hrs, and a white precipitate will separate out. Pour off the upper layer solution and the precipitate is dried in vacuum. The required compound (I) of high purity is then obtained.

Results after treatment of rat's ischemic cerebral-vascular/reperfusion injury with the compound (I) are as follows. Use ischemic cerebral-vascular/reperfusion SD rat model to observe treatment effects of the Compound (I). Experiments showed that intravenous injection of 50 mg/kg, 10 mg/kg, or 2 mg/kg of the Compound (I) can decrease area of cerebral tissue necrosis, caused by cerebral arteria embolisms/reperfusion, can decrease production of oxygen radicals, can relieve cerebral tissue edema and decrease the lowering of cerebral electric amplitude, and improve behavior obstruction of the tested animals. The cure effects showed dosage dependent. Main drug effect experiments showed at the same time that the cure effects of Compound (I) are better than those of the positive control drug—Nimodipine.

The actual implementation shall be as follows.

Animals for Experiment

Prepare cerebral arteria embolisms/reperfusion injury rat model according to Longna method. To bring the animal into a state of narcosis, give an intravenous injection of urethane (0.4 ml/100 g weight). Maintain body temperature of the rat at 37±0.5° C. (anal temperature). Let the rat lie on a plate with face toward the ceiling. Make a cut at the right middle of its neck. By means of microsurgery techniques, separate left neck communis and its branches. Isolate arteria carotis externa. By means of electric solidification, cut off occipital arteria, thyroid superia gland arteria, and arteria phyrynix externa, all of which are setting out from arteria carotis externa. Isolate arteria carotis externa further towards the head end. Tie the arteria carotis externa at a place as far as possible. Clamp the beginning part of the arteria carotis externa to make it close with an artery clamp. Tie a loose knot (with 5-0 silk thread going through the arteria carotis externa) at a place between the artery clamp and the tying thread. At a place close to the knot, cut to block the arteria carotis externa. Put into the arteria carotis externa a 3-0 nylon thread, which is 5 cm long and has a drumstick-like head. Tie a fast knot on the silk thread on the arteria crotis externa to avoid bleeding. Remove the arteria clamp. Push the nylon thread slowly into the arteria carotis externa. Adjust direction in order to insert the nylon thread into cranial chamber. When resistance can be felt, it means that cerebral fore arteria is reached. Calculating from the beginning part of arteria carotis interna, the length of nylon thread, that has been inserted into is generally 20~21 mm. At this position, the beginning part of arteria in the brain is blocked, and at the same time the branch blood vessels from fore cerebral arteria, arteria carotis interna, and rear brain arteria are blocked. Then tie three more knots near the loose node on the arteria carotis externa's left part of the thread. Suture the cut. Introduce the nylon thread out of the cut in the skin in order to form reperfusion when it is pulled out. When pulling out the nylon thread, it should be done gently. When resistance is felt, the pulling should be stopped. It means the blocking expanded head of the nylon thread has got back into the left end of the arteria carotis externa, and reperfusion has been made.

Test Grouping

For groups of experiment, the compound (I) and control drugs were all administered by means of intravenous injection. The volumes of injection were the same.

The animals were divided into groups with random.

It was set that reperfusion would be formed after obstruction and ischemia of 1 hour. Indexes were observed after 5 hours when reperfusion was made. The groups for experiments were as follows:

| Group | Number of animals | Indexes observed | Dosage compound (I) mg/kg | Nimodipine μg/kg | Time of injection 1. minutes after obstruction | 2. minutes after reperfusion |
|---|---|---|---|---|---|---|
| I | 10 | 1,2,3 | 50 | 10 | 10 | 5 |
| II | 10 | 1,2,3 | 50 | 10 | 30 | 30 |
| III | 10 | 1,2,3 | 10 | 20 | 10 | 5 |
| IV | 10 | 1,2,3 | 2 | 40 | 10 | 5 |
| V | 10 | 4,5 | 50 | 20 | 10 | 5 |

Indexes Observed
1. Measurement of Area of Cerebral Embolisms.

Open the cranium and take the whole brain. Remove olfactory bulbus, cerebellum, and cerebral stem. Slice the brain corona into 6 pieces of equal thickness. The numbering is 1, 2, 3, 4, 5, 6 in the direction from front end to occipital end. The front end of each slice is named side A, and the rear end of each slice—side B. Put number 2, 3, 4 slices into 1% TTC (triphenytetrazolium chloride). When using it, it is dissolved with distilled water and kept off from light). Keeping light off, dye it in water bath for 10 minutes. The dehydrogenase contained in normal tissue reacts with TTC and shows red. As for obstructed tissue, because of loss of dehydrogenase, there is no reaction of it with TTC. So, the color shows white. The degree of whiteness, which reflects the reaction between tissue and TTC, also reflects the degree of denaturalization and necrosis of obstructed cerebral tissue. The area of obstructed cerebral tissue was measured with a fully automatic image analysis system (Model IPAS-C, Kontror Co, Germany). The degree of denaturalization and necrosis of obstructed cerebral tissue can be shown using gray levels by means of that system. The greater is the gray level, the greater is the degree of seriousness. For this experiment, the average value of those measured of slices 2 and 3 were taken as the measured result for each animal's area of obstruction.

2. Measurement of Water Content in Brain Tissue:

With Gotoh method as reference, take out the rat brain rapidly. Weigh right and left brain hemispheres with electronic balance of 1/100,000 respectively. Then they were put into oven to dry until the weights remain constant. Weigh the brain hemispheres again respectively. Calculate water content according to the following formula:

Water content (%)=[(wet weight−dry weight)/wet weight]×100%

3. Pathological Exam:

After dyeing the brain slices with TTC, put them into 10% formalin to solidify. After procedures of de-watering, wax immersing, wrapping and embedding, slicing, etc, normal haematoxylin eosine (HE) was used to do dyeing to show necrosis of nerve cells. Myelin staining was used to show if nerve fibers are demyelinated, and to show degree of demyelination.

4. Scanning Record of Electroencephalogram

One needle-type electrode was placed at top forehead. Another electrode was placed under rat's ear skin of obstructed side as reference electrode. Electroencephalogram change outside of skin before and after obstruction was recorded with 8-lead physiological recorder made by Japan Optical-Electric Co.

5. Bio-Chemical Test 38 rats were used. After making cerebral ischemia/reperfusion injury, the rats were randomly divided into groups of contrast (equal volume of physiological salt-water), Nimodipine treatment (40 μg/kg), and Compound (I) treatment (50 mg/kg). Ten minutes after cerebral ischemia was made, and reperfusion was made. After another 5 minutes, drug was given iv under tongue. 60 minutes after cerebral ischemia was made, reperfusion was made. After another 5 hours, rat brains were stripped off rapidly according to Gotoh Method. Right and left brain hemispheres were weighed respectively, and were kept in fridge at −70° C.

The tissue to be measured (about 0.3~0.5) were washed clean with physiological salt-water. Then cold distilled water was used to prepare homogenate on a glass blender. Then centrifugal machine was set at 1,500 rpm to work for 15 minutes, the temperature being 0° C. Supernatant was removed to carry out content measurement for malonis aldehyde (MDA) and activity of superoxide dismutase (SOD).

(1) SOD measurement (pyrogallol self-oxidation method): Take a 15 ml test tube. Orderly put into the tube are 4.5 ml of pH 8.2 Tris-HCL buffer solution, 4.3 ml of double distilled water, 0.1 ml of sample homogenate e solution, 0.1 ml of 7 mmol/L pyrogallol (0.1 ml of 10 mmol/L HCL is added into blank tube). Calibrate the blank tube for zero. Change of absorbance is measured under conditions of: ultra-violet spectrophotometer (UV 1601 PC, Shimatsu Co., Japan), wavelength of 325 nm, and slit of 2. Then activity units are calculated according to the following formula:

Tissue homogenate $SOD(u/g$ cerebral tissue$)$=(control tube−sample tube)/control tube/0.5×1/cerebral tissue weight $(g)$ (2) MDA measurement according to the procedures listed in the following table

| Reagent (ml) | Test tube | Blank tube | Standard tube |
|---|---|---|---|
| 10% homogenate | 0.2 | — | — |
| MDA standard solution | — | — | 0.2 |
| 8.1% SDS | 0.2 | 0.2 | 0.2 |
| 20% acetic acid buffer solution | 1.5 | 1.5 | 1.5 |
| 1% TBA | 1.5 | 1.5 | 1.5 |
| Distilled water | 1.0 | 1.0 | 1.0 |

Shake to make the sample uniform. Heat in 95° C. water bath for 60 min. After cooling down, put it in a centrifuge and run it at 3,000 rpm for 15 min. Take the supernatant to measure its absorbance with spectrophotometer at wavelength of 532 nm. Then get the MDA content on standard curve of MDA.

6. With Longa Method as reference and 5 hours after reperfusion, observe change of behaviors and carry out evaluation. Evaluation standards are as follows. No behavior change—0 score. Fore right limb cannot stretch straight—1 score. Inclination to the right side but no active circling—2 scores. Right side walking—3 scores. Rotation to the right at the original place—4 scores. Right paralysis—5 scores.

Results of Experiments

1. Influence on Infarction Area.

Results of experiments showed that 2~50 mg/kg of Compound (I) could relieve cerebral tissue injury caused by cerebral ischemia/reperfusion, and could decrease embolism area of cerebellum tissue. The cure effect depends on dosage. For the group of Nimodipine treatment, there was a trend of decrease of area of cerebellum tissue infarction, but only for groups treated with great dosage, there was significant statistics difference ($p<0.01$). However, the general cure effect was weaker than that of the group treated with Compound (I).

2. Influence on Brain

Results of experiments showed that for salt-water group, when cerebral arteria was first blocked for 1 hour and at the time of 5 hours after reperfusion, amplitude of electroencephalogram decreased significantly. A dosage of 50 mg/kg and 10 mg/kg could improve electroencephalogram significantly. The decrease of amplitude of electroencephalogram lowered significantly ($p<0.01$). For the group of 2 mg/kg dosage treatment, there was a tendency of improvement of electroencephalogram, but there was no significant statistics difference. For the group treated with Nimodipine, when the dosage was 40 kg, there was an appearance of improvement of electroencephalogram ($p<0.05$).

3. Influence on Pathological Changes of Nerve Cells and Nerve Fibers

Results of experiments showed that all dosages of intravenous injection of Compound (I) of 50 mg/kg, 10 mg/kg, and 2 mg/kg could decrease the number of nerve cells of necrosis and could relieve the degree of denaturalization of nerve fibers. Its protection effects were dosage-dependent, and were better than those of Nimodipine.

4. Influence on Change of Behavior

Results of experiments showed that the scores for the physiological salt-water contrast group were 3.3±1.0. For the Nimodipine group, the scores were 2.9±1.2 ($p>0.05$, compared with physiological salt-water). For the group treated with Compound (I), serious behavior obstruction caused by cerebral injuries could be significantly relieved. There was no statistics significant difference between the two groups of Nimodipine treatment and salt-water.

5. Influence on SOD Activity and MDA Content

Results of experiments showed that for the physiological salt-water SOD activity decreased significantly. It decreased significantly from 70.30±24.7 u/g of normal contrast group (false surgery group) to 46.7±16.6 u/g ($p<0.05$). Comparing the group of Compound (I) and the group of Nimodipine with normal contrast group, there was no significant statistics difference ($p<0.05$) for SOD activity. The content of MDA for physiological salt-water group was 87.7±27.5 nmol/mg tissue weight. Comparing with normal contrast group (false surgery group) (60.0±14.8 mmol/mg tissue weight), it increased significantly ($p<0.01$). For the groups treated with Compound (I) and Nimodipine, MDA content could be lowered nearly to that of the normal group. They were 65.8±19 and 67.0±21.8 nmol/mg tissue weight (compared with normal group $p>0.05$).

6. Influence on Water Content of Cerebral Tissue

Results of experiments showed that intravenous injection of Compound (I) could significantly lower water content increase of cerebral tissue in blocked area, caused by cerebral ischemia/reperfusion. Although 20 μg/kg of Nimodipine had a trend to decrease it, there was no significant statistics difference when compared with group of physiological salt-water.

CONCLUSION

Results of experiments showed that intravenous injection of 50 mg/kg, 10 mg/kg, and 2 mg/kg of Compound (I) could significantly lower area of necrosis of cerebral tissue caused by cerebral ischemia/reperfusion, could relieve nerve cell necrosis, could relieve degree of edema of cerebral tissue, could decrease production of oxygen free radicals and degree of decrease of amplitude of electroencephalogram, and could improve animals' behavior obstruction. The cure effects were dependent on dosage, and were better than that of active contrast drug Nimodipine.

Summarization of the above-mentioned data showed that Compound (I) has significant cure effects for cerebral tissue injury and necrosis, caused by cerebral embolism/reperfusion. It can be used to cure acute ischemic cerebral-vascular diseases.

Results of acute toxicity test for Compound (I) were:

| Mouse | Intravenous injection of medicine | $LD_{50}$ 356.18 mg/kg |
|---|---|---|
| | 95% confidence margin: | 346.01~366.64 mg/kg |
| | Intramuscular injection | $LD_{50}$ 583.96 mg/kg |
| | 95% confidence margin: | 564.77~603.79 mg/kg |

Results of Chronic Toxicity Test for Compound (I) were:

Rats were treated with compound (I) by iv injection for 14 days, which caused mainly inflammation of tail vein inner membrane. Degree of injury was correlated positively with dosage of drug used. For 10 and 30 mg/kg, there was minor local stimulation; 100 mg/kg were a poisonous dosage. Results of three kinds of experiments (if it causes disability, cancer, and mutation) showed that compound (I) does not have these side effects. Bone marrow micronucleus test showed that compound (I) does not induce the forming of bone marrow polychromatic erythrocyte nuclei. In summary, compound (I) has good cure effects for cerebral ischemia/reperfusion injury, while there is little toxicity. Clinically, it can be used for acute ischemic cerebral-vascular diseases, suffering from apoplexy, cerebral bleeding, cerebral cell injury and necrosis caused by cerebral ischemia/reperfusion resulted from cerebral embolism. Pharmacological experiments show that Compound (I) has characteristics different from that of $Ca^{2+}$ channel blocking drug used clinically at present. The latter has blocking effect only for electric-voltage-dependent $Ca^{2+}$ channel; it has very little effect on $Ca^{2+}$ channel controlled by acceptors. On the contrary, Compound (I) has blocking effect only for $Ca^{2+}$ channel controlled by acceptors. Increase of $Ca^{2+}$ internal flow related with acute ischemic cerebral-vascular diseases is mainly related with $Ca^{2+}$ channel controlled by acceptors. Compound (I) has just this new way of effectiveness. It interferes with common channels (increase of $Ca^{2+}$ internal flow, and $Ca^{2+}$ overload in cells), which cause cerebral cells die. Thus, goal of cure effect can be achieved for cerebral ischemia/reperfusion injury and cerebral infarction. Therefore, its cure effects are good.

When compound (I) is used to treat acute ischemic cerebral-vascular diseases, the following treatment plans are usually adopted. Compound (I) is made into powder injection preparation or solution for injection. Intramuscular or intravenous injection of 10~30 mg once is done every 12 hours. 7~14 days represent 1 cycle of treatment. Compound (I) can be given orally, but the dosage should be doubled. Compound (I) can also be prepared together with other drugs to make compound preparation, for example, with embolism-solvent (such as tpA, etc), with fibrinolytic drugs (such as snake venom plasmin), with citicoline, etc. Effects of treatment enhancement or even coordination cure effects can be achieved.

When glucose radical of Compound (I) on position 3 decreases by one, there will be similar effects. That is, the chemical is: 20-(S)-protopanaxadiol-3-[O-β-D-glucopyranosyl (1→2)-β-D-glucopyranosyl]-20-O-β-D-glucopyranoside. If one glucose radical of compound (I) on position 3 is replaced by another mono-saccharine, for example, isodulcitol, there will be similar effects.

Compound (I) can also be prepared into succinate derivatives (for example, potassium, sodium) for use as a drug.

In the following, there is further explanation for this invention with reference to the examples.

EXAMPLE 1

Take the corpus radicis and radix fibrosa of pseudo-ginseng. Crush the roots. For 1 kg of raw drug powder, use industrial alcohol containing 85% ethanol, to immerse the powder overnight, and filter. For the residue, do hot extraction three times with 85% alcohol, each time being 3 hours. Combine the filtrates; and after recovering ethanol, extract the concentrated filtrates with n-butanol to obtain coarse total saponins, for which gradient elution is done on 65×1300 mm chromatographic column (1200 g of column chromatography silicon gel of 100~200 mesh is filled in). The elution is done with elution solutions of different proportions in the following order: chloroform (83%)-methanol (16%)-water (1%), chloroform (76%)-methanol (22% o)-water (2%), chloroform (68%)-methanol (28%)-water (4%), chloroform (65%)-methanol (30%)-water (5%), and chloroform (61%)-methanol (33%)-water (6%) etc. Collect eluates of 550 ml as one portion, and test them on TLC. Combine those having similar $R_f$ values. After recovering the solvents, obtain a concentrate in the form of decocted paste. After dissolving the concentrate in the form of decocted paste with a little methanol, it is separated and purified on $C_{18}$ reversed phase column. Then another elution is done with elution solutions of different proportions in the following order: methanol (60%)-water (40%), methanol (65%)-water (35%), methanol (70%)-water (30%), methanol (80%)-water (20%), methanol (85%)-water (15%), methanol (100%)-water (0%). Collect eluates of 100 ml as one portion, and test them with TLC. Combine those having similar $R_f$ values. After recovering methanol and doing concentration, do the same reversed phase column purification as above for the second time. After recovering methanol from the collected eluates, allow it to stand for 24 hours. White precipitate will be separated out. Remove off the supernatant, dry the precipitate in vacuum at 40° C., and a single substance (3 g, 98% pure) will be obtained.

Physical and chemical property tests and element analysis were carried out for the substance. Also done were its mass spectra, infrared and ultraviolet spectrum, $^1H$ and $^{13}C$ nuclear magnetic resonance tests. The conditions and results were:

Physical and chemical properties: white or a little yellow powder. Melting point—209~214° C. Very easy to dissolve in lower alcohol, acetone, chloroform, and hot water.

Specific rotation: $[a]_D^{22}$+19.38° (c=1.03, MeOH)

Element analysis: $C_{48}H_{82}O_{18}\cdot 3H_2O$, catd. (%) C 57.62, H 8.79, mesd (%)C 57.32, H 8.93, FAB-MS (m/e): 969[M+Na]$^+$, 946[M]$^+$, 789[M+Na-180]$^+$, 721[789-68]$^+$, 627[789-163+H]$^+$, 587[789-179-Na]$^+$, 407[789-341-$H_2O$-Na]$^+$, 203[180+Na]$^+$, 145[180-2$H_2O$+H]$^+$, 109 (base peak)

IR ($v^{KBr}_{max}$cm$^{-1}$): 3395[s, b, v (OH, $H_2O$)], 2945, 2882[s, v ($CH_3$, $CH_2$, CH)], 165 [m, b, v (C=C)+v(OH) ], 1454 [m, v ($CH_3$)+v($CH_2$)], 1384[m, v ($CH_3$)+v(CH)], 1082, 1032[s, v (C—O)]

$^1$H-NMR[$C_5D_5N$, spectrum bandwidth 5037.5 Hz (10 ppm)]. There are altogether 82 proton-peaks, where ginseng saponin-enin has 50, and glucose and xylose contain 32. In between 0.8~1.6 ppm there are 8 methyl groups. 0.789, 1.0707, 1.245 ppm peaks are peaks 18-$CH_3$, 29-$CH_3$, 28-$CH_3$ peaks, joined on at position 8 and position 4 carbon. 0.84 (2×$CH_3$) and 1.598 ppm (3×$CH_3$) peaks are 19-$CH_3$, 30-$CH_3$, and 26-$CH_3$, 27-$CH_3$, 21-$CH_3$ peaks joined on at position 25,20 carbon. 3.24 ppm peak is tertiary carbon proton one of joining oxygen at position 3. 4.04 peak contains tertiary carbon proton one of joining hydroxyl at position 12. 5.24 peak is one of alkene at position 24. 3.8~5.3 ppm peak group is mainly CH, $CH_2$ proton peak of glucose and xylose. 5.7~7.9 ppm wide peak group is 11 hydroxyl proton peaks. Its hydrogen spectrum data is as follows. δ: 0.65(1H, d, J=11.5 Hz, 5-H), 0.73(1H, q, J=11 Hz, 1—H), 0.789(3H, s, 18-$CH_3$), 0.84(6H, s, 19, 30-$CH_3$), 1.00(3H, t, J=12 Hz, $CH_3$), 1.07(3H, s, 29-$CH_3$), 1.21(1H, t, J=7.5 Hz, —H), 1.245(3H, s, 28-$CH_3$), 1.34(3H, m, 6, 11, 15-H), 1.52(3H, m, 1, 9, 15-H), 1.598(9H, s, 21, 26, 27-$CH_3$), 1.81(3H, m, J=10.5 Hz, 2, 16, 22-H), 1.94(2H, t, J=10 Hz, 13, 16-H), 2.16(1H, d, J=12.5 Hz, 2-H), 2.21(1H, m, 23-H), 2.34(1H, t, J=11 Hz, 22-CH), 2.44(1H, s(br), 23-H), 2.50(1H, q, J=9 Hz, 17-H), 3.24(1H, dd, J=8, 3.5 Hz, CH at position 3 attached to oxygen), 3.87(1H, s, OH), 3.94(1H, t, J=8 Hz, 20-glc-2H), 4.04(4H, q, J=8 Hz, 12-H, OH, glc-2H), 4.11(2H, t, J=9 Hz, 3-glc-2H, 20-glc-3H), 4.18(3H, m, J=8 Hz, CH), 4.24(4H, m, J=9 Hz, CH), 4.41(3H, m, J=11.5 Hz, CH), 4.50(1H, d, J=11 Hz, CH), 4.86(1H, d, J=7.5 Hz, 20-glc-1H), 5.12(1H, d, J=8 Hz, glc-1H), 5.24(1H, t, 24-H), 5.29(1H, d, J=7.5 Hz, 3-glc-1H), 5.61(1H, s, CH), 5.71(1H, s(br), OH), 6.08(1H, s(br), OH), 6.28(1H, s(br), OH), 7.03(3H, s(br), OH), 7.22(3H, s(br), OH), 7.49(1H, s(br), OH), 7.84(1H, s(br), OH)

$^{13}$C-NMR[$C_5D_5N$, 500 MHz, spectrum width 26016.3 Hz (ppm)]. There are a total of 48 effective peaks. 8 $CH_3$ carbon peaks, 12 $CH_2$ carbon peaks, 22 CH carbon peaks, and 6 quaternary carbon peaks are determined by DEPT spectrum, where 30 carbon peaks are of saponin, and the rest 18 belong to 3 pyranose saccharine. Its carbon spectrum data is follows: δ: 15.88(q, $CH_3$), 16.19(q, $CH_3$), 16.50(q, $CH_3$), 17.27(q, $CH_3$), 17.72(q, $CH_3$), 18.35(t, $CH_2$), 22.37(q, $CH_3$), 23.17(t, $CH_2$), 25.70(q, $CH_3$), 26.55(t, $CH_2$), 26.63(t, $CH_2$), $^28.00$(q, $CH_3$), 30.71(t, $CH_2$), 30.71(s, C), 35.06(t, $CH_2$), 35.96(t, $CH_2$), 36.81(s, C), 39.11(t, $CH_2$), 39.60(s, C), 39.93(s, C), 49.29(d, CH), 50.08(d, CH), 51.35(s, C), 51.65 (d, CH), 56.32(d, CH), 62.65(t, $CH_2$), 62.73(t, $CH_2$), 62.73 (t, $CH_2$), 70.18(d, CH), 71.38(d, CH), 71.54(d, CH), 71.54 (d, CH), 74.97(d, CH), 76.85(d, CH), 77.67(d, CH), 77.88(d, CH), 78.05(d, CH), 78.05(d, CH), 78.16(d, CH), 78.97(d, CH), 83.17(d, CH), 83.26(d, CH), 88.94(d, CH), 98.12(d, CH), 104.93(d, CH), 105.76(d, CH), 125.82(d, CH), 130.86 (s, C).

UV (λ max, nm): 200.80

By means of hydrolyzing with 7% $H_2SO_4$ and 50% acetic acid, it can be proved that sapogenin is panaxadiol, and the saccharine fraction is glucose. There is 1 molecular of glucose attached at position C20.

EXAMPLE 2

Take main root and fibrous root of ginseng. The rest is the same as example 1.

EXAMPLE 3

Take main root and fibrous root of pseudo-ginseng. The first gradient elution solution is chloroform (80%~55%)-ethyl acetate (15%~30%)-water (5%~15%). The polarity increases gradually. Reversed phase column purifying gradient elution solution is ethyl (60%~100%)-water (40%~0%). The polarity decreases gradually.

For every example of this invention, rather high purity of single substance is achieved by column chromatographic elution done twice.

This invention is not limited to the above-mentioned examples.

What we claim is:

1. A method for extracting a compound of a formula (I),

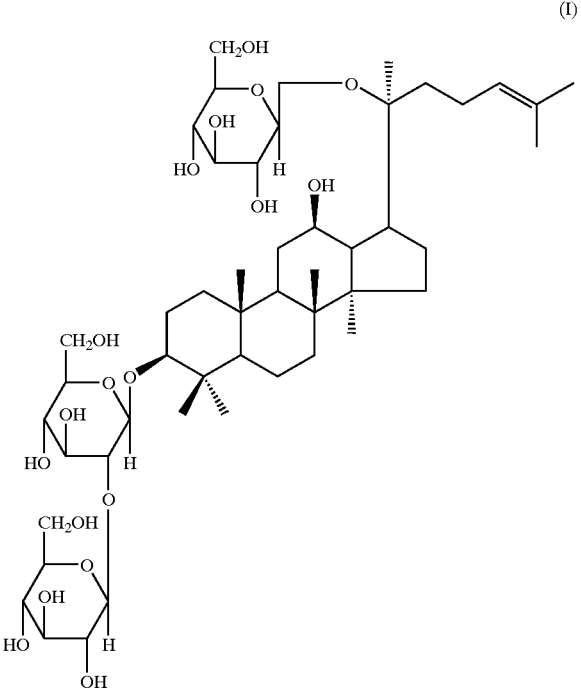

(I)

comprising:
   (1) providing a corpus radicis and/or radix fibrosa of a ginseng spp. plant, ginseng or pseudo-ginseng, crushing roots, cold extracting once with industrial alcohol, hot extracting 0–3 times, combining the filtrates, and then extracting with n-butanol to obtain coarse total saponins;
   (2) separating the coarse total saponins with gradient elution solutions by silica gel column chromatography, the gradient elution solutions comprising chloroform, methanol and optionally water, and then condensing a desired fraction to obtain a condensed solution in a form of a decocted paste; and
   (3) dissolving the condensed solution with an appropriate amount of methanol, separating and purifying the solution with the gradient elution solutions on a reverse phase column, the gradient elution solutions comprising methanol and water, and collecting the desired fraction; recovering the methanol from the collected desired fraction, and allowing the fraction to stand for more than 24 hrs to separate out a white precipitate, and drying the precipitate to obtain a single substance.

2. A method according to claim 1, wherein the gradient elution solutions of silica gel column chromatography are chloroform (85%–0%)-methanol (15% –30%)-water (0%–10%), with polarity increasing gradually.

3. A method according to claim 1, wherein the gradient elution solutions of silica gel column chromatography are chloroform (83%)-methanol (16%)-water (1%), chloroform (76%)-methanol (22%)-water (2%), chloroform (68%)-methanol (28%)-water (4%), chloroform (65%)-methanol (30%)-water (5%), and chloroform (61%)-methanol (33%)-water (6%).

4. A method according to claim 1, wherein the gradient elution solutions of a reversed phase column chromatography are methanol (50%–100%) and water (50%–0%), with polarity decreasing gradually.

5. A method according to claim 1, wherein the gradient elution solutions of a reversed phase column chromatography are provided in the following order: methanol (60%)-water (40%), methanol (65%)-water (35%), methanol (70%)-water (30%), methanol (80%)-water (20%), methanol (85%)-water (15%), and methanol (100%)-water (0%).

6. A method according to claim 1, wherein the ginseng is a North America ginseng.

7. A method according to claim 2, wherein the gradient elution solutions of silica gel column chromatography are chloroform (83%)-methanol (16%)-water (1%), chloroform (76%)-methanol (22%)-water (2%), chloroform (68%)-methanol (28%)-water (4%), chloroform (65%)-methanol (30%)-water (5%), and chloroform (61%)-methanol (33%)-water (6%).

8. A method according to claim 6 wherein the gradient elution solutions of a reversed phase column chromatography are provided in the following order: methanol (60%)-water (40%), methanol (65%)-water (35%), methanol (70%)-water (30%), methanol (80%)-water (20%), methanol (85%)-water (15%), and methanol (100%)-water (0%).

9. A method according to claim 1, wherein the substance has a purity of at least 95%.

10. A method according to claim 1, wherein the substance has a purity of at least 98%.

11. A method according to claim 4, wherein the reversed phase column chromatography is $C_8$–$C_{18}$ reversed phase column chromatography.

12. A method according to claim 5, wherein the reversed phase column chromatography is $C_8$–$C_{18}$ reversed phase column chromatography.

13. A method according to claim 8, wherein the reversed phase column chromatography is $C_8$–$C_{18}$ reversed phase column chromatography.

* * * * *